(12) United States Patent
Herold

(10) Patent No.: US 6,702,740 B2
(45) Date of Patent: Mar. 9, 2004

(54) BARTHOLIN GLAND SPECULUM

(76) Inventor: Karen Herold, 9023 Cynthia St. #5, Los Angeles, CA (US) 90069

(*) Notice: Subject to any disclaimer, the term of this patent is extended or adjusted under 35 U.S.C. 154(b) by 0 days.

(21) Appl. No.: 10/084,295

(22) Filed: Feb. 25, 2002

(65) Prior Publication Data

US 2002/0169363 A1 Nov. 14, 2002

Related U.S. Application Data

(60) Provisional application No. 60/271,110, filed on Feb. 23, 2001.

(51) Int. Cl.[7] .................................................. A61B 1/32
(52) U.S. Cl. ...................................................... 600/220
(58) Field of Search ................................ 600/184, 188, 600/190, 196, 220, 222

(56) References Cited

U.S. PATENT DOCUMENTS

| | | |
|---|---|---|
| 351,548 A | 10/1886 | Watson |
| 361,087 A | 4/1887 | Schenck |
| 596,399 A | 12/1897 | Fox |
| 693,345 A | 2/1902 | Bearer |
| 786,457 A | 4/1905 | McGinnis |
| 1,217,745 A | 2/1917 | Gracey |
| 2,661,735 A | 12/1953 | Davis |
| 2,809,628 A | 10/1957 | Jonas |
| 3,565,061 A | 2/1971 | Reynolds |
| 3,575,163 A * | 4/1971 | Gasper .................. 600/222 |
| 3,752,149 A | 8/1973 | Ungar et al. |
| 3,815,585 A * | 6/1974 | Fiore ..................... 600/222 |
| 6,258,024 B1 * | 7/2001 | van Der Weegen ......... 600/115 |
| 6,280,379 B1 * | 8/2001 | Resnick .................. 600/220 |

FOREIGN PATENT DOCUMENTS

| | | |
|---|---|---|
| CH | 337611 | 5/1959 |
| DK | 59995 | 7/1942 |
| FR | 2 600 519 A1 | 12/1987 |
| FR | 2 668 357 A2 | 4/1992 |
| IT | 250936 | 7/1929 |

OTHER PUBLICATIONS

Catalog of George Tiemann & Co.'s Surgical Instruments, pp. 300, 439, 441, 446 and 449—dated 1889.
Catalog of Chas Truax Tru Greene & Co, pp. 1469, 1470 and 1475, dated 1893.
Catalog of John Reynders & Co, pp. 319, 320 and 321, dated 1895.
Brochure of Gynecologic History, Examination & Diagnostic Procedures, pp. 544 and 621, with pictures reproduced from 1983 handbooks.
Catalog of Leisegang—Specialty Products Division, pp. 1, 16, 17, 27 and Leisegang Specialty Products Catalog brochure page dated Jun. 18, 1999.

* cited by examiner

Primary Examiner—Cary E. O'Connor
(74) Attorney, Agent, or Firm—Christie, Parker & Hale, LLP

(57) ABSTRACT

A surgical speculum for use for vaginal insertion that may be used for treatment of a bartholin gland is provided. The speculum has a pair of blades in facing relation to one another and each having a distal end and a proximal end. The blades each undergo an angular transition at a point between their distal ends and their proximal ends. At least one of the blades has an opening in its center that extends on either side of the angular transition.

14 Claims, 5 Drawing Sheets

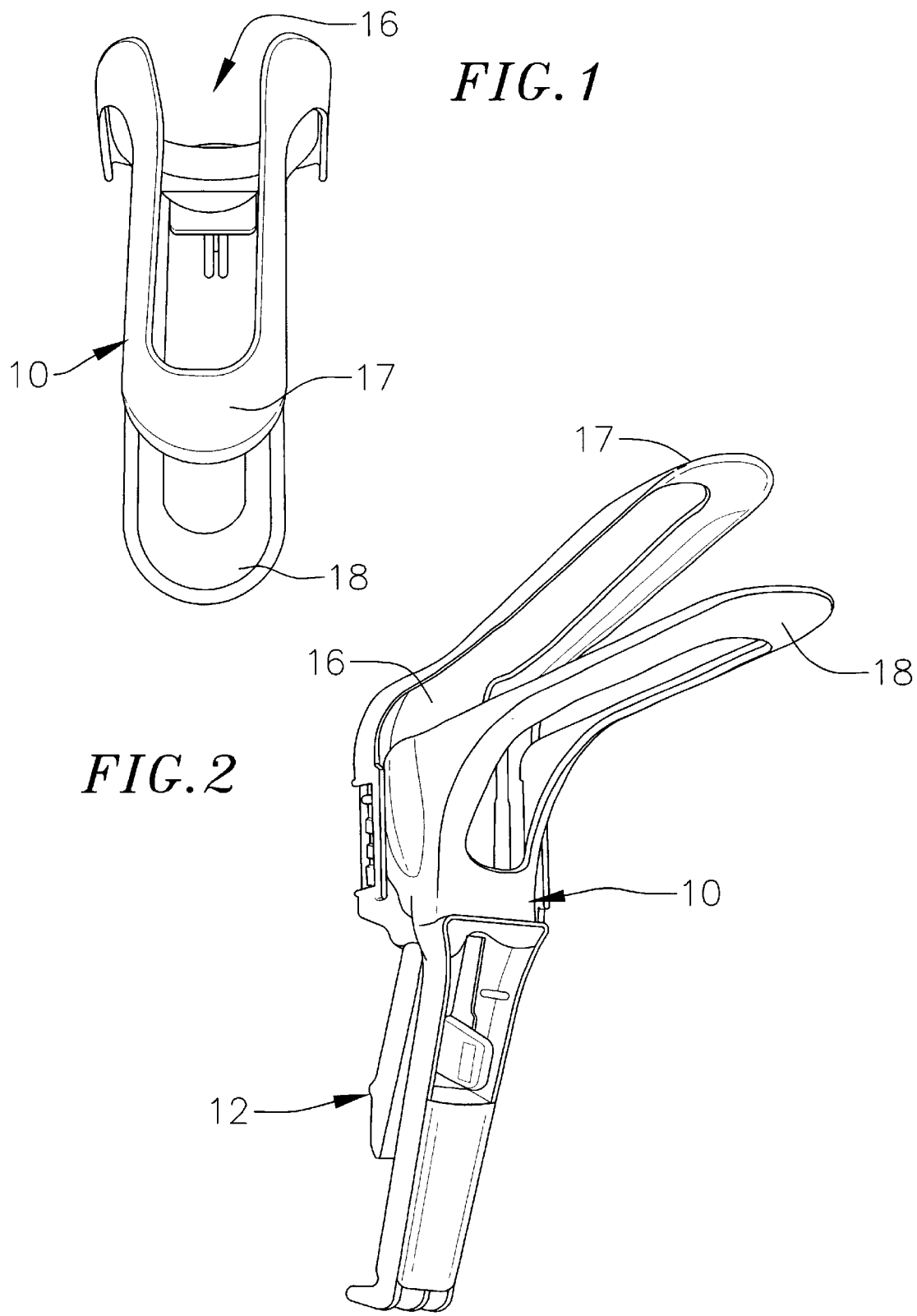

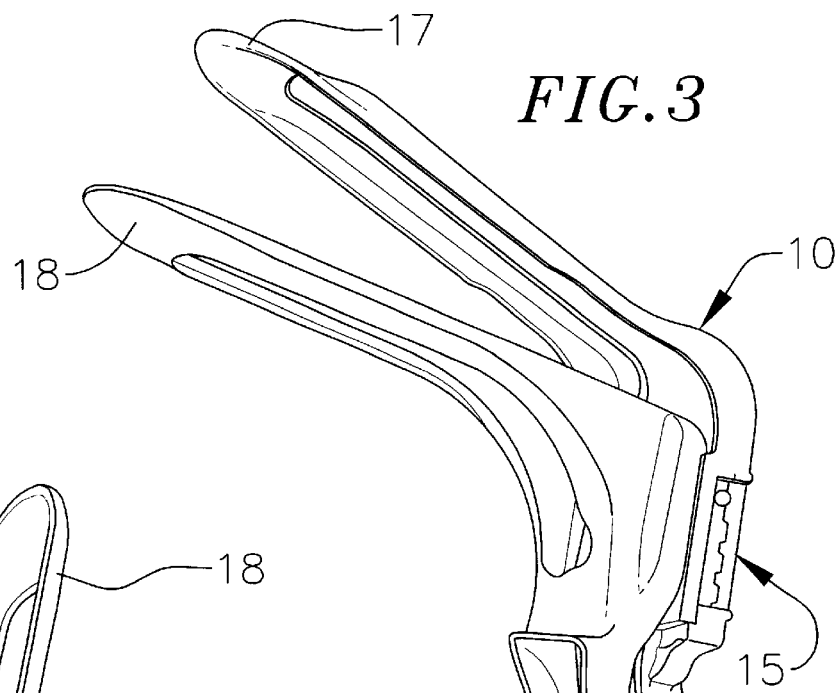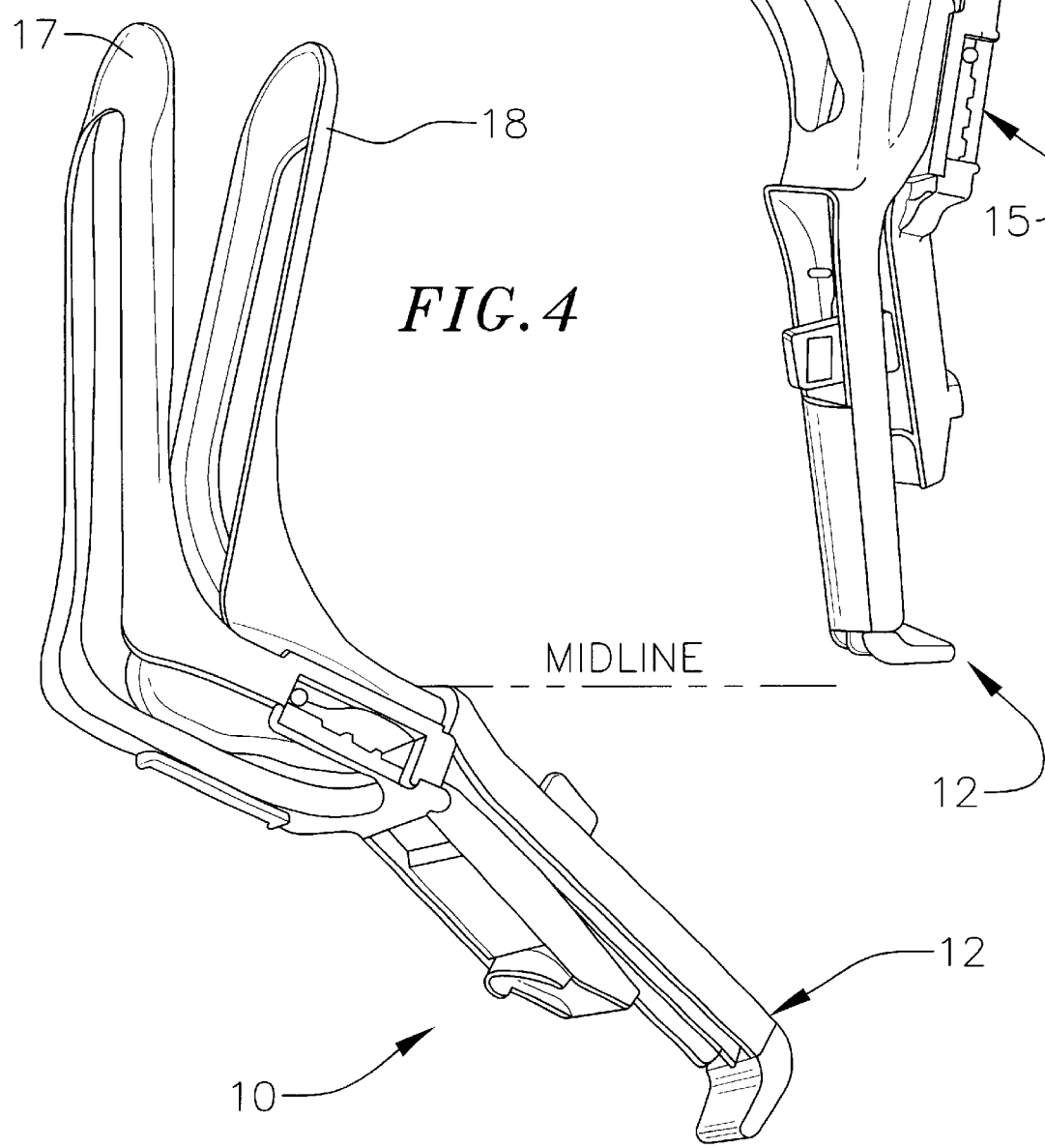

BARTHOLIN GLAND SPECULUM

CROSS-REFERENCE TO RELATED APPLICATION(S)

The present application claims priority to U.S. Provisional Patent Application No. 60/271,110, filed Feb. 23, 2001, which is hereby incorporated by reference as if set forth in full herein.

TECHNICAL FIELD OF THE INVENTION

The present invention is directed to a new surgical speculum. In particular, it is directed to a speculum to be used for bartholin gland isolation and visualization during treatment, surgery, irrigation and drainage, or placement of an indwelling catheter.

BACKGROUND OF THE INVENTION

Heretofore there have been no instruments used specifically for bartholin gland isolation and visualization. Currently, bartholin gland surgery, treatment, and/or irrigation and drainage is accomplished solely by the surgeon isolating and/or retracting the bartholin gland and anterior vaginal walls manually during a procedure. The opposite hand is used for surgery or treatment. This is an awkward and archaic surgical procedure. Accordingly, a device and method are needed to free both hands of the surgeon for treatment or surgery.

SUMMARY OF THE INVENTION

The present invention provides a surgeon with a device that adequately and properly provides bartholin gland isolation and visualization; thus freeing both hands to accomplish the required treatment or surgery. In one embodiment, it enables the surgeon to treat, surgically irrigate, drain, or insert an indwelling catheter without having to manipulate or retract the bartholin gland manually.

In various embodiments, it may also provide a stable sterile field during bartholin gland treatment and/or surgery and provide a speculum with such an architecture as to allow a complete view of and not obscure the surgical field.

In a particular embodiment, the speculum of the present invention has an adjustable handle providing a means for maintaining its blades in alignment. This would accomplish lateral retraction of the anterior vaginal wall to such an extent as to enable easy access to the bartholin gland. The speculum handle in such an embodiment may also be inverted from the midline so as to avoid contact with the patients legs when the speculum is inserted as intended.

BRIEF DESCRIPTION OF THE DRAWINGS

To complete the understanding of the nature and scope of the present invention, reference is had to the following descriptive embodiments of the invention taken in conjunction with the accompanying drawings, wherein:

FIG. 1 is a top view of a speculum constructed in accordance with the present invention looking down on its handle from above its blades;

FIG. 2 is a perspective side view of the speculum;

FIG. 3 is the opposite perspective side view from FIG. 2.

FIG. 4 is a further perspective side view showing the relationship of the speculum handle to the midline;

DETAILED DESCRIPTION OF THE INVENTION

Figure 5:
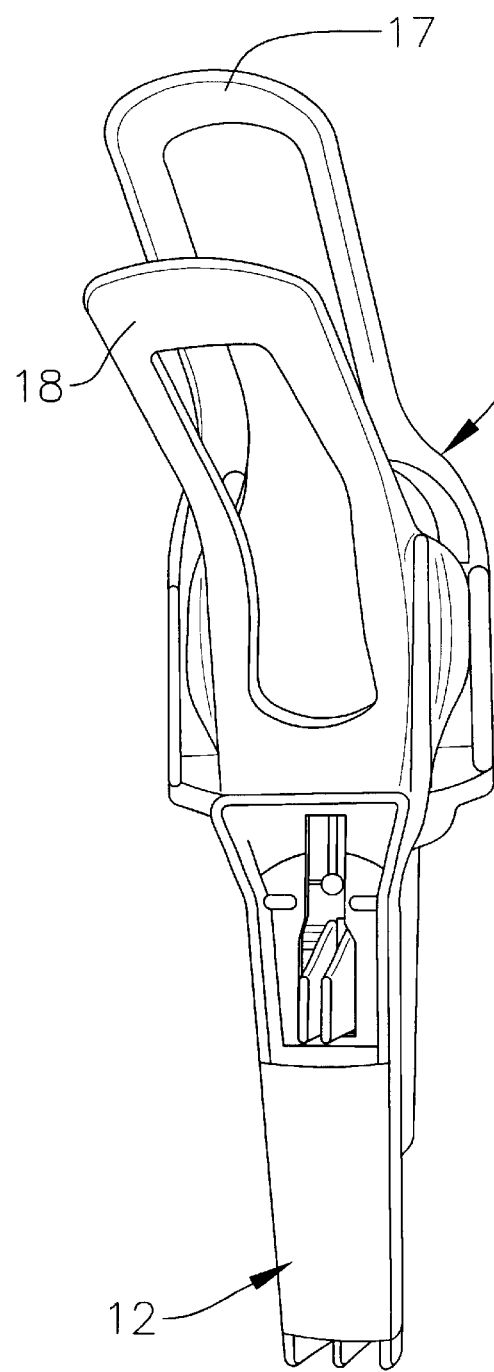
FIG. 5 is a perspective bottom view of the speculum.

FIG. 1 shows a top view of a speculum 10 that has a superior cut out 16. That is, as shown in FIG. 1, an upper blade 17 of the speculum is open in its center, which opening extends back toward the proximal end of the upper blade near a handle 12 of the speculum. Thus, the proximal end of the upper blade is cut out to allow a clear field of view during insertion and use of the speculum. Similarly, a lower blade 18 of the speculum is open in its center, which opening extends back toward the proximal end of the lower blade through the transition to the handle. (See FIGS. 2 and 3). Although, for ease of reference, the blades have been referred to herein as "upper" and "lower," it should be understood that typically the speculum will be inserted for lateral retraction so that the blades will be at either side of the vaginal wall as inserted for side-to-side retraction.

FIG. 4 shows the handle of the speculum inverted approximately 20 degrees from the midline (the line forming generally a 90 degree angle with the "upper" blade) of the generally perpendicular intersection of the speculum blades thereby eliminating contact with the patient's legs during treatment or surgery. The terminal end of the speculum handle 12 is turned toward the midline of the speculum blades thereby eliminating contact with the patient's legs. Thus, even though the speculum is typically inserted with the blades at either side, interference with the patient's legs is minimized.

Bilateral speculum blades 17 and 18 provide lateral retraction. Adequate length of the blades provides reach to the posterior fornix of the vagina. Bilateral openings 14 and 19 provide adequate bartholin gland isolation and visualization for treatment or surgical modalities. Either one or both of these openings may be further enlarged, particularly at the end toward the handle after the transition from the blade toward the handle to further improve visualization and access to the bartholin gland. Normally, such enlargement would be achieved by expanding the outer dimensions of the proximal end of a blade. Both openings may be enlarged to allow use of the speculum with the handle facing toward either side of the patient to accommodate particular surgeon preferences.

Within a forward length 15 of the speculum handle 12 is a ratcheting mechanism which provides ability to widen the anterior vagina thereby increasing visualization and treatment capabilities of the surgeon. Any mechanism that will allow the two blades of the speculum to be slid laterally apart from one another, thereby increasing the spacing between the two blades, and then to hold in that spaced apart position for a desired time period may be incorporated into the speculum. The embodiment illustrated employs outwardly facing pins 20 at either side of the lower portion of the speculum, which are received in tracks 22 at either side of the upper portion of the speculum. These pins may then ratchet along the tracks in response to thumb pressure on the handle part of the upper portion. (See FIG. 7).

Figure 6:
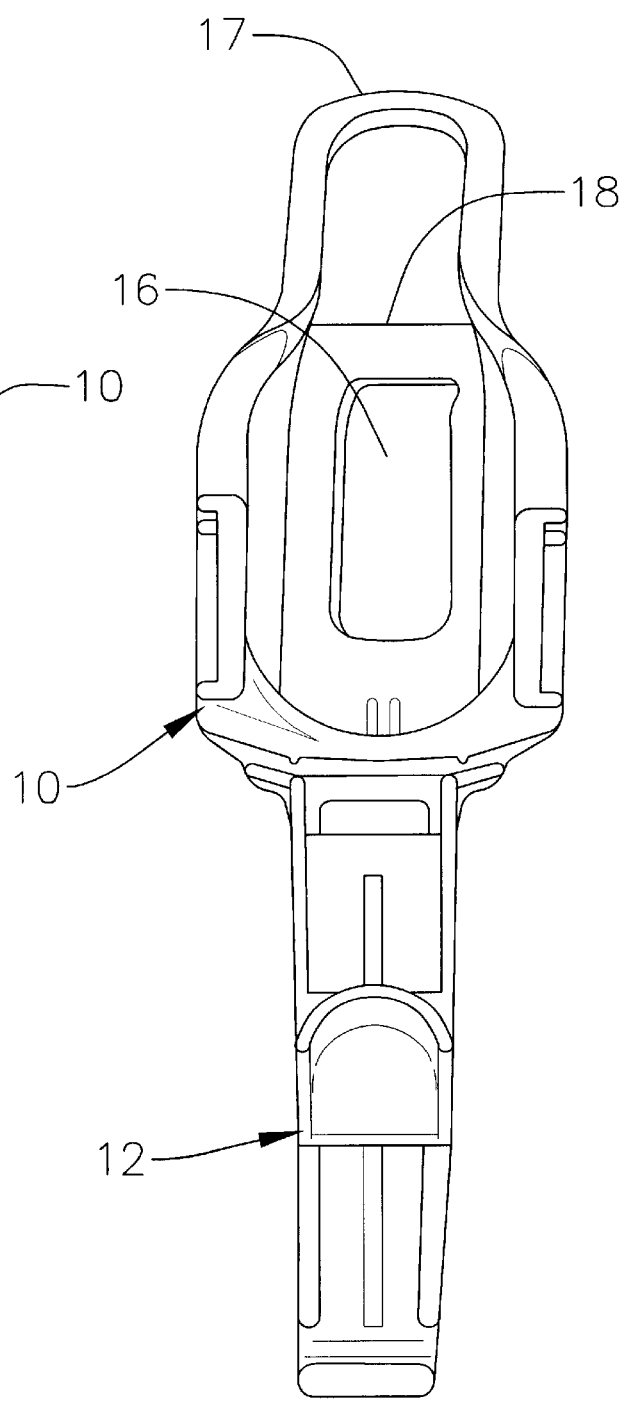
FIG. 6 is a top view through the anterior of the speculum.
Figure 7:
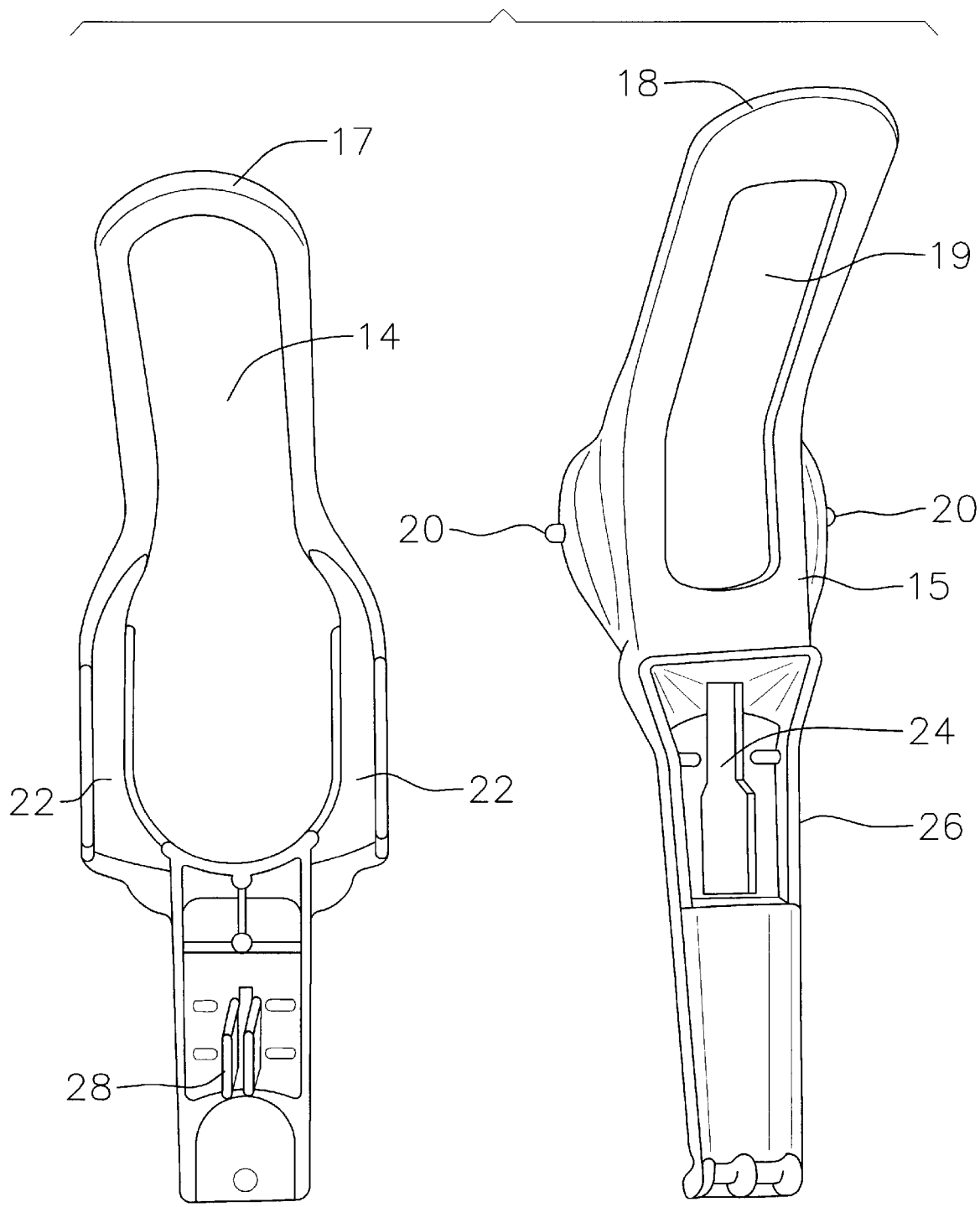
FIG. 7 is a bottom view of the two parts of the speculum separated from one another.
Figure 8:
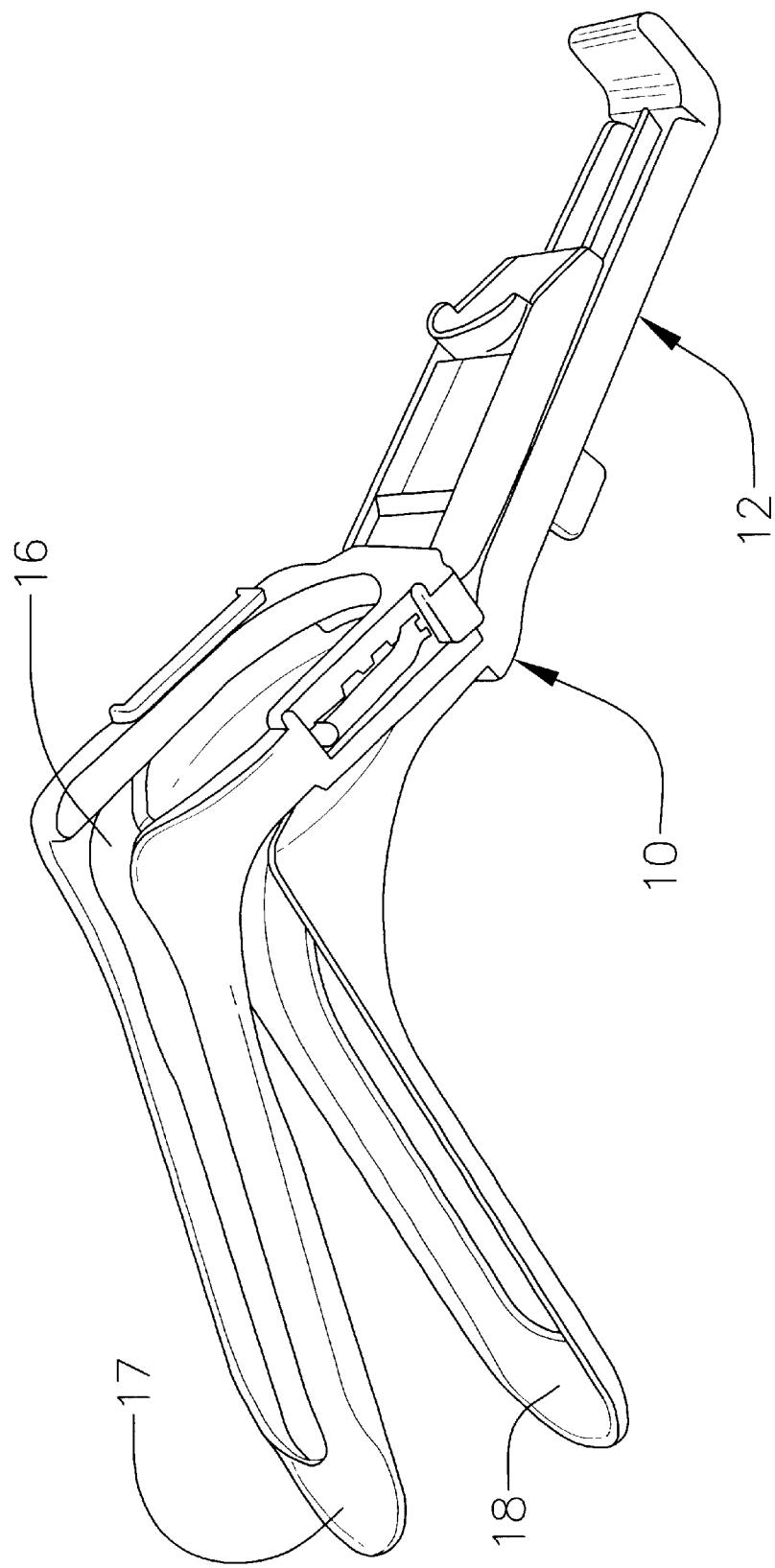
FIG. 8 is a further perspective side view of the speculum showing a superior cut out.

FIG. 2 and FIG. 3 both show opposite side views of the speculum blade cut outs which provide maximum anterior vaginal wall and bartholin gland isolation and visualization. FIG. 5 shows a bottom view of the speculum while FIG. 6 shows a view through the anterior of the speculum. FIG. 7 illuminates both separate components of the speculum blades. The lower portion of the speculum has a through slot 24 extending lengthwise along a mid length 26 of its handle part. The through slot receives a tab portion 28 extending from the handle part of the upper portion of the speculum thereby joining the two portions of the speculum together, but allowing them to slide over one another along their handle parts, as well as allowing some degree of pivoting rotation of the blades about the pins 20 so that the distal ends of the blades can be pivoted toward each other and away from each other. FIG. 8 provides yet another view of the cut out enabling the surgeon adequate room for instrumentation and treatment of the bartholin gland.

The speculum of the present invention may be formed of stainless steel or any other sturdy material able to be sterilized so as to allow for repeated use. Alternatively, the speculum may be fabricated from plastic, such as by molding, and may then be an expendable instrument after one use. If to be expendable, it may be packaged in a sterile condition and removed from its wrapper at time of use and after use it may be discarded.

For purposes of description, particular embodiments of the invention have been shown. However, it will be apparent to those skilled in the art that many changes and modifications may be made herein without departing from the true spirit of the invention. Thus, the scope of the invention should be determined in accordance with the following claims.

What is claimed is:

1. A vaginal speculum comprising:
   a pair of blades in facing relation to one another, each blade having a distal end and a proximal end;
   a handle positioned at the proximal ends of the pair of blades and connecting the blades to one another;
   the pair of blades each undergoing an angular transition at a point between the distal and proximal ends; and
   at least one of the blades having an opening in its center that extends on either side of the angular transition, the opening having a size and configuration to provide anterior vaginal wall and bartholin gland isolation and visualization during insertion and use of the speculum.

2. A vaginal speculum according to claim 1 wherein the opening is wider in diameter on the side of the angular transition toward the proximal end of the at least one of the blades.

3. A vaginal speculum according to claim 1 wherein the blades are connected to one another in a manner that allows the blades to be moved literally with respect to one another.

4. A vaginal speculum according to claim 1 wherein the blades are connected to one another in a manner that allows the blades to rotate with respect to one another about a point near their proximal ends.

5. A vaginal speculum according to claim 1 wherein the handle is positioned at an angle with respect to the proximal ends of the blades.

6. A vaginal speculum according to claim 1 wherein the handle is positioned at an angle of approximately 20 degrees with respect to a midline of the speculum.

7. A vaginal speculum according to claim 1 wherein the speculum is made of a sturdy, sterilizable material.

8. A vaginal speculum according to claim 7 wherein the material is stainless steel.

9. A vaginal speculum according to claim 1 wherein the speculum is made of plastic.

10. A vaginal speculum according to claim 1 wherein the speculum is packaged in a sterile condition and may be disposed after a single us.

11. A vaginal speculum comprising:
    a pair of blades in facing relation to one another, each blade having a distal end and a proximal end;
    a handle positioned at the proximal ends of the pair of blades and connecting the blades to one another;
    the pair of blades each undergoing an angular transition at a point between the distal and proximal ends; and both blades have having an opening in their centers that extend on either side of the angular transition.

12. A vaginal speculum according to claim 11 wherein the opening in each blade is wider in diameter on the side of the angular transition toward the proximal end of the blades.

13. A surgical speculum for use for treatment of a bartholin gland comprising:
    a pair of blades in facing relation to one another and each having a distal end and a proximal end, adapted for side-by-side vaginal insertion of the distal ends;
    a handle located at the proximal ends of the blades and connecting the blades to one another;
    the blades undergoing an angular transition at a point between their distal and proximal ends;
    at least one of the blades having an opening in its center, the opening extending on either side of the angular transition and having a size and configuration to provide anterior vaginal wall and bartholin gland isolation and visualization during insertion and use of the speculum; and
    the handle positioned at an angle to the proximal end of the blades so as to minimize interference with a patient's legs during insertion of the blades.

14. A method for visualization and/or treatment of a bartholin gland comprising:
    inserting vaginally a distal end of a pair of blades side by side;
    retracting laterally the pair of blades;
    the blades undergoing an angular transition at a point between their distal end and a proximal end of each blade;
    at least one of the blades having an opening in its center, the opening extending on either side of the angular transition and having a size and configuration to provide anterior vaginal wall and bartholin gland isolation and visualization during insertion and use of the blades to provide a field for the bartholin gland.

* * * * *